United States Patent [19]

Lowrie

[11] Patent Number: 4,473,501

[45] Date of Patent: Sep. 25, 1984

[54] DIHYDRO AZINO ISOQUINOLINES

[75] Inventor: Harman S. Lowrie, Glenview, Ill.

[73] Assignee: G. D. Searle & Co., Skokie, Ill.

[21] Appl. No.: 329,789

[22] Filed: Dec. 11, 1981

Related U.S. Application Data

[63] Continuation-in-part of Ser. No. 260,547, May 4, 1981.

[51] Int. Cl.³ .................. C07D 217/14; A61K 31/47
[52] U.S. Cl. ................... 260/192; 546/141; 546/143; 548/229; 424/258
[58] Field of Search ............... 546/141, 143; 424/258; 548/229

[56] References Cited

U.S. PATENT DOCUMENTS

| | | | |
|---|---|---|---|
| 3,753,994 | 8/1973 | Diana | 546/143 |
| 3,946,009 | 3/1976 | Wasson et al. | 544/408 |
| 4,009,170 | 2/1977 | Diana | 546/143 |
| 4,065,456 | 12/1977 | Kazuyuki | 546/141 |
| 4,073,909 | 2/1978 | Troxler et al. | 424/258 |
| 4,115,575 | 9/1978 | Frei et al. | 544/408 |
| 4,137,318 | 1/1979 | Eberlain et al. | 424/258 |
| 4,212,877 | 7/1980 | Köppe | 546/148 |

FOREIGN PATENT DOCUMENTS

| | | | |
|---|---|---|---|
| 536744 | 5/1952 | Canada | 546/143 |
| 47-21421 | 6/1972 | Japan | 424/272 |
| 0106981 | 8/1975 | Japan | 546/141 |
| 0117783 | 9/1975 | Japan | 546/141 |
| 7413858 | 4/1975 | Netherlands | 424/258 |
| 307873 | 8/1955 | Switzerland | 546/143 |

*Primary Examiner*—Donald G. Daus
*Assistant Examiner*—G. Hendricks
*Attorney, Agent, or Firm*—John J. McDonnell

[57] ABSTRACT

The invention provides novel 1,5-substituted isoquinoline derivatives of formula I which are useful in the treatment of hypertension.

5 Claims, No Drawings

DIHYDRO AZINO ISOQUINOLINES

BACKGROUND OF THE INVENTION

This application is a continuation in part of U.S. application Ser. No. 260,547, filed May 4, 1981.

(a) Field of Invention

The present invention provides novel organic compounds. In particular, this invention relates to novel 5-substituted isoquinolines of formula I which exhibit vasodialator and antihypertensive activity and as such will be useful in the treatment of hypertension.

Hypertension is a condition which is often characterized by the arterioles exhibiting abnormal resistance to the flow of blood and is usually associated with an abnormal increase in systolic, diastolic, and mean arterial blood pressures. Arterial pressure is the product of cardiac output times the total peripheral resistance. An increase in either of these two factors therefore can cause hypertension. However, in most types of hypertension one finds the total peripheral resistance is greatly increased while the cardiac output is near to normal. Disease states exhibiting hypertension included renal hypertension, Goldblatt's hypertension, tumor-induced hypertension, and essential hypertension where etiology is unknown. Elevation of blood pressure has been induced in animals through CNS, neurogenic, renal and adrenal mechanisms, large amounts of sodium chloride, as well as by administration of certain drugs. Although all these mechanisms may play a part, heredity is a predisposing factor, suggesting a genetic contribution of some kind. Irrespective of the etiology of the condition, the elevated pressure per se accelerates a number of degenerative processes that shorten life expectancy. Goodman and Gillman: The Pharmacological Basis of Therapeutics, 4th Ed. pgs 728-763.

Treatment of hypertension may be by treatment of the etiology of the hypertension or by the introduction of drugs that exhibit a direct effect on blood pressure. A patient would be considered for treatment with pharmacologic agents by an attending physician and include conditions where the patient has hypertension, where the diastolic pressure is persistently above 95 mm Hg or where there is vascular disease related to the hypertensive state. These states may be readily determined by an attending physician of ordinary skill. The Merck Manual 12 Ed. 465-471 (1972).

(b) Description of the Prior Art

A wide variety of drugs and methods of treating hypertension exists. The main categories of activity for antihypertensives are: diuretics, beta-adrenegic blockers, centrally acting alpha agonists, vasodilators, alpha receptor antagonists, norepinephrine-depleting agents and adrenergic neuron-blocking drugs. For a detailed description of the drugs in these classes see, for example, Cecile, Textbook of Medicine 15th Ed. pgs 1212-17 (1979).

Of particular interest is U.S. Pat. No. 4,093,725 by Roe et al. Roe describes substituted hydrazinophthalazines which are active as beta-adrenergic blocking agents and as vasodilators. These compounds are chemically distinct however from the compounds of the present invention.

SUMMARY OF THE INVENTION

The present invention particularly provides a compound according to formula I wherein $R_1$ is:
  (a) hydrogen;
  (b) alkyl of 1 to 6 carbon atoms inclusive;
  (c) hydroxy;
  (d) oxo;
  (e) —NH—NH$_2$;
  (f) =N—N=R$_4$; or
  (g) mercapto;
wherein $R_4$ is:
  (a) =CR$_5$R$_6$; or
  (b) cycloalkylene of 4 to 8 carbon atoms, inclusive;
wherein $R_5$ and $R_6$ are:
  (a) hydrogen; or
  (b) alkyl of 1 to 6 carbon atoms inclusive, $R_5$ and $R_6$ each being the same or different;
wherein $R_2$ is:
  (a) —CH(OR$_7$)—CH$_2$—NR$_8$R$_9$; or
  (b) oxazolidinone of formula II;
wherein $R_7$ is:
  (a) hydrogen; or
  (b) alkyl of 1 to 6 carbon atoms inclusive;
wherein $R_8$, $R_9$, and $R_{10}$ are:
  (a) hydrogen;
  (b) alkyl of 1 to 6 carbon atoms inclusive; or
  (c) dialkoxy phenylalkyl; each alkoxy portion and the alkyl portion having from 1 to 6 carbon atoms, inclusive; $R_8$, $R_9$, and $R_{10}$ each being the same or different;
wherein $R_3$ is:
  (a) halogen;
  (b) hydrogen;
  (c) alkyl of 1 to 6 carbon atoms inclusive; or
  (d) alkoxy of 1 to 6 carbon atoms inclusive;
wherein $R_{11}$ is:
  (a) hydrogen; or
  (b) oxazolidinylmethyl of formula III; with the proviso that there is an $R_{11}$ only when there is saturation between carbons 1 and 2 of formula 1.

Examples of alkyl of 1 to 6 carbon atoms inclusive, are methyl, ethyl, propyl, butyl, pentyl, and hexyl and the isomeric forms thereof.

Examples of alkoxy of 1 to 6 carbon atoms, inclusive, are methoxy, ethoxy, propoxy, butoxy, pentoxy and hexoxy and the isomeric forms thereof.

The test procedure used to determine anti-hypertensive and vasodialator activity is as follows:

Spontaneously hypertensive male rats, 11 to 16 weeks old, are used. These are the SHR/Cox strain, obtained from Laboratory Animal Supply Co., Indianapolis, Ind. 46241. The rats are maintained at least 1 week in house prior to use. Initial systolic blood pressure is measured by a caudal plethysmograph or by venal catheter probe immediately before administration of compound to be treated. Blood pressure readings are repeated at 4 and 24 hours after intragastric administration of the compound. A dose of test compound is rated active if the post-treatment blood pressure of the treated rats are significantly depressed (P§0.05) from the initial pressure reading. Statistical comparisons are made using the non-paired Student's t test. The spontaneously hypertensive rat exhibits a genetically linked hypertention that is similar in many respects to essential hypertension in man. A clinical correlation exists between this test and drugs already shown useful in the treatment of human hypertension, eg. guanethidine, apresoline and hydrochlorothiazide.

By virtue of this anti-hypertensive activity the compounds of formula I are useful in treating hypertension symptoms in humans and animals. A physician or veterinarian of ordinary skill could readily determine a subject who is exhibiting such symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally, vaginally in such forms as suppositories or bougies; they may also be introduced in the form of eye drops, interparenterally, subcutaneously, or intramuscularly, using forms known to the pharmaceutical art. In general, the preferred form of administration is orally.

An effective but non-toxic quantity of the compound is employed in treatment. The dosage regimen for preventing or treating hypertension by the compounds of this invention is selected in accordance with a variety of factors including the type, age, weight, sex, and medical condition of the mammal, the severity of the hypertension, the route of administration and the particular compound employed. An ordinarily skilled physician or veterinarian will readily determine and prescribe the effective amount of the anti-hypertensive agent to prevent or arrest the progress of the condition. In so proceeding, the physician or veterinarian could employ relatively low dosages at first, subsequently increasing the dose until a maximum response is obtained.

Initial dosages of the compounds of the invention are ordinarily in the area of 1 mg/kg up to at least 50 mg/kg by injection. When other forms of administration are employed equivalent doses are administered.

The compounds of this invention can also be administered as pharmacologically acceptable acid addition salts such as the hydrochloride, hydrobromide, hydroiodide, sulfate, phosphate, acetate, propionate, lactate, maleate, malate, succinate, tartrate and the like. Additionally, the compounds of this invention may be administered in a suitable hydrated form.

The formulas on Charts B, C and D describe the process for making the compounds of the instant invention.

The intermediate alcohol, formula XIV is prepared by the following method. Epichlorohydrin is converted to 3-benzyloxypropyleneoxide, formula XI, by reaction of the alkoxide of benzyl alcohol. After purification the intermediate formula XI is allowed to react with an alkyl amine, giving an N-substituted-3-benzyloxy-2-hydroxypropylamine, formula XII. Reaction of the resultant amino alcohol with ethyl chloroformate gives the 5-(benzyloxymethyl)-3-substituted-2-oxazolidinone, formula XIII, from which the benzyl group is removed by hydrogenolysis. The resultant, alcohol, formula XIV, is activated for further reaction by conversion to 5-(p-toluenesulfonyloxymethyl)-3-substituted-2-oxazolidinone, of formula XV. Two routes can be used for the preparation of the compound of formula XXIV, (5-[1,2-dihydro-1-(isopropylazino)isoquinolin-5-yloxymethyl]-3-substituted-2-oxazolidinone). In the first method the alkali metal salt of 5-hydroxyisoquinoline is allowed to react with the tosylate of formula XV giving 5-(isoquinolin-5-yl oxymethyl)-3-substituted-2-oxazolidinone, formula XXI. This intermediate is oxidized with hydrogen peroxide in acetic acid to the corresponding N-oxide, formula XXII. Subsequent reaction of formula XXII with phosphorus oxychloride gives the chloro intermediate of formula XXIII. The isopropylazino formula XXIV compound, (or other alkylazino compounds) are derived from formula XXIII by sequential reaction with hydrazine and then acetone (or other ketones.)

In the second method a mixture in solvent of 1,5-dihydroxyisoquinoline, the tosylate formula XV, and powdered sodium hydroxide gives the intermediate formula XXXI, which is converted to the corresponding thio compound formula XXXII by reaction with phosphorus pentasulfide. Reaction of this intermediate with hydrazine, followed by reaction with acetone, produces a compound of formula XXIV, identical in all respects to that prepared by the first method.

Compound of formula, XXIV prepared by either method, is solvolyzed using potassium hydroxide in refluxing isopropyl alcohol. Neutralization with acid and purification produces a compound of formula XXV 1-[1,2-dihydro-1-(isopropylazino) isoquinolin-5-yloxy]-3-alkylamino-2-propanol.

DESCRIPTION OF THE PREFERRED EMBODIMENTS

The operation of this invention is further elaborated by the representative examples below:

Example 1

3-benzyloxy propyleneoxide (formula XI of Chart B)

To 432 g (4.0 mole) of benzyl alcohol in 2.0 liters of dimethoxyethane is added portionwise 192 g (4.0 mole) of a 50% suspension of NaH in mineral oil while stirring under nitrogen. The mixture is stirred one hour at room temperature and then is heated slowly to reflux for about one half hour until hydrogen evolution ceases. The mixture is cooled in an ice bath and 1,480 g (16 mole) of epichlorohydrin is added rapidly while maintaining the temperature between 30° C. and 40° C. After stirring two hours, the mixture is refluxed overnight and then cooled and filtered. The filtrate is concentrated at 50° to 70°/20 mm. the residue is dissolved in $CH_2Cl_2$, washed twice with dilute hydrochloric acid then dried over sodium sulfate, filtered and concentrated. The residue is distilled to yield 355 g (54%) of a water-white oil having a boiling point of 75° to 80° C./0.2 mm.

Analysis calculated for $C_{10}H_{12}O_2$: C, 73.14; H, 7.37. Found: C, 72.97; H, 7.27.

Example 2

N-isopropyl 3-benzyloxy-2-hydroxypropylamine (formula XII of Chart B: $R_{10}$isopropyl)

To 490 g (3.0 mole) of title compound Example 1 which is dissolved in one liter of methanol is added with stirring 974 g (16.5 mole) of isopropylamine while maintaining the temperature below 30° C. by cooling in an ice bath; the solution is stirred overnight at room temperature then it is concentrated first on a steam bath and finally at 40° to 60° C./0.5 mm. An oil results having a boiling point of 112° to 113° C./0.1 mm.

Example 3

5-(benzyloxymethyl)-3-isopropyl-2-oxazolidnone (formula XII of Chart B: $R_{10}$is isopropyl)

To 595 g of title compound example 2 and 410 ml of triethylmine dissolved in 2 liters of anhydrous ether is added while stirring 326 g (2.94 mole) of ethylchloroformate keeping the temperature at below 30° C. The mixture is stirred overnight at room temperature, then is washed thoroughly with water, once with dilute hydrochloric acid, once with dilute sodium hydroxide, dried and concentrated by boiling. Distillation of the residue affords 450 g (68%) of a light yellow oil having a boiling point of 190° to 195° C./0.8 mm.

Example 4

5-hydroxymethyl-3-isopropyl-2-oxazolidinone (formula XIV of Chart B: $R_{10}$ is ispropyl)

A total of 450 g (1.81 mole) of title compound Example 3 is reduced with hydrogen at room temperature in five equal batches, each in 75 ml of ethanol using 1.0 g of 10% Pd/C at 60 psi. The solutions are filtered, combined and concentrated at 40°-60° C./20 mm; the residue is dissolved in two liters of ether and on cooling furnishes 245 g (85%) of white crystals having a melting point of 60°-63.5° C. Additional crops may be obtained from the filtrate.

Analysis calculated for $C_7H_{13}NO_3$: C, 52.81; H, 8.23; N, 8.80. Found: C, 52.77; H, 8.15; N, 8.92.

Example 5

5-(p-Toluenesulfonyloxymethyl)-3-isopropyl-2-oxazolidione (formula XV of Chart B: $R_{10}$ is isopropyl)

To 50 g (0.315 mole) of the title compound of Example 4 dissolved in 120 ml of pyridine and 250 ml of $CH_2Cl_2$ is added 84 g (0.441 moles) of p-toluenesulfonyl chloride. After the mixture stands overnight at 0° C. the solution is stirred for two days at room temperature, then is filtered and the filtrate washed thoroughly with dilute hydrochloric acid and with dilute sodium carbonate. It is then dried over calcium sulfate and the solvent removed at 20° C./20 mm. The residue crystalized from cyclohexane as white matted needles in a yield of 78.0 g (79%) and a melting point of 96°-98° C.

Analysis calculated for $C_{14}H_{19}NO_5S$: C, 53.66; H, 6.11; N,4.47. Found: C, 53.69; H, 6.09; N, 4.54.

Example 6

In like manner, by substituting t-butylamine in Examples 1 through 5 the reactions may be carried through to the corresponding tosylate obtained as a white crystalline powder having a melting point of 105°-108° C. isolated from acetone-toluene.

Analysis calculated for $C_{15}H_{21}NO_5S$: C, 55.03; H, 6.46; N, 4.28; S, 9.79. Found; C, 55.05; H, 6.51; N, 4.36; S, 9.72.

Example 7

Using the procedure of Examples 1 through 5 and substituting 3,4-dimethoxyphenethylamine, the corresponding tosylate is obtained as a white powder having a melting point of 91°-94° C. from a toluene-Skellysolve-B solvent system.

Analysis calculated for $C_{21}H_{25}NO_7S$: C, 57.92; H, 5.79; N, 3.22; S, 7.36. Found, C, 58.07; H, 5.85; N, 3.26; S, 7.01.

Example 8

5-(Isoquinolin-5-yloxymethyl)-3-isopropyl-2-oxazolidinone (formula XXI Chart C: $R_{10}$ is isopropyl)

To a suspension of 0.9 g (0.022 mole) of NaH (57% in mineral oil) and 60 ml of hexamethylphosphoramide cooled below 10° C. under nitrogen is added with stirring 3.2 g (0.022 moles) of 5-hydroxyisoquinoline. After 15 minutes gas evolution ceases, and 6.2 g (0.02 mole) of title compound, Example 5, is added. The mixture is allowed to warm to room temperature and stands for 2 ½ days. Upon dilution to 500 ml with water and cooling the product crystallizes and is filtered off and recrystalized from ethyl acetate-Skellysolve B solvent system furnishing 3.56 g (62%) of white needles having a melting point of 119° to 120° C.

Analysis calculated for $C_{16}H_{18}N_2O_3$: C, 67.11; H, 6.33; N, 9.78. Found: C, 67.02; H, 6.51; N, 9.80.

Example 9

5-(Isoquinolin-5-yl N-oxide)oxymethyl-3-isopropyl-2 oxazolidinone (formula XXII of Chart C: $R_{10}$ is isopropyl)

A solution of 0.50 g (1.75 mmole) of title compound Example 8 and 1.0 ml (10 mmole) of 30% hydrogen peroxide in 5 ml of acetic acid is allowed to stand for four days at room temperature. After diluting with water and making basic with dilute sodium hydroxide, crystals are filtered off, dried, and recrystalized from a 50% ethanol-ethyl acetate solvent to yield 0.25 g (47%) of shiny matted needles having a melting point of 192°-193° C.

Analysis calculated for $C_{16}H_{18}N_2O_4$: C, 63.56; H, 6.00; N, 9.27. Found: C, 63.25; H, 6.05; N, 9.00.

Example 10

5-(1-Chloroisoquinolin-5-yloxymethyl)-3-isopropyl-2-oxazolidinone (formula XXIII of Chart C: $R_1$ is Cl, $R_{10}$ is isopropyl)

To a solution of 9.13 g (0.0302 mole) of title compound Example 9 in 700 ml of $CH_2Cl_2$ which is cooled to 0° C., is added 25 mL of $POCl_3$; this is allowed to warm to room temperature and stand for 2 ½ days. It is then poured onto ice/ammonium hydroxide and stirred for 2 hours, the layers are then separated. The $CH_2Cl_2$ is washed twice with water, dried by shaking with saturated sodium chloride solution and filtered through anhydrous potassium carbonate. The solvent is stripped and the light yellow powder dried at 20° C.

Analysis calculated for $C_{16}H_{17}ClN_2O_3$: C, 59.90; H, 5.34; N, 8.73; Cl, 11.05. Found: C, 59.82; H, 5.28; N, 8.63; Cl, 11.20.

This material contains about 5 to 10% (by NMR) of the 4-cloro isomer. Recrystallization from acetone-ether or from benzene-Skellysolve C gives yellow crystals having a melting point of 128° to 133° C. of unchanged purity. Since the 4-cloro isomer does not appear to react in the subsequent example this material is used without further purification.

Example 11

5-[1,2-dihydro-1-(1-methylethyl)azinoisoquinolin-5-yloxy methyl]-3-(1-methylethyl)-2-oxozolidinone (formula XXIV of Chart C: $R_1$ is $=N-N=C(CH_3)_2$, $R_{10}$ is isopropyl)

A solution of 21.0 g (0.065 mole) title compound example 10 and 40 ml of anhydrous hydrazine in 250 ml of dry pyridine is refluxed under a nitrogen atmosphere for eight hours. The solution is cooled, diluted with ethanol and stripped at 40° C.; this process is repeated three times. The residue is dissolved in acetone and stirred overnight with 5.6 g (equimolar) of sodium acetate; the sodium chloride is filtered off and the filtrate evaporated at 40° C. The residue is dissolved in $CH_2Cl_2$, washed with dilute sodium hydroxide, dried potassium carbonate and then evaporated. Crystallization of the residue from an acetone-ether solvent system affords 4.73 g (20%) of yellow powdery crystals having a melting point of 176° to 180° C. which on recrystallization with little loss from benzene yields light yellow plates having a melting point of 179° to 181° C. after drying at 100° C./1 mm.

Analysis calculated for $C_{19}H_{24}N_4O_3$: C, 64.02; H, 6.79; N, 15.72. Found; C, 4.10; H, 6.83; N, 15.62.

Dilution of the original filtrate with ether furnishes 9.6 grams of additional material having a melting point of 170° to 180° C. The mother liquors are combined, stripped and 9.1 gram of red oil is produced and chromatographed in methylene chloride on 100 g of neutral silca gel. Elution with increasing percentages of acetone furnished in the following order: about 1% unreacted 1-chloro isomer, and about 10% of 4-chloro isomer. The 4-chloro isomer recrystallized from an acetone Skelly-D solvent system furnished tan prisms, melting point 106°–108° C.

The free hydrazine analog of formula XXIV 5-[1-hydrazino isoquinolin-5-yloxymethyl]-3-(1-methylethyl)-2-oxazolidinone may be isolated before conversion to the acetone hydrazone by several recrystallizations from methanol as a slightly light and air-unstable yellow crystaline powder having a melting point of 178° to 182° with decomposition.

Example 12

5-[1-(cyclopentylazino)-1,2-dihydrol isoquinolin-5-yloxymethyl]-3-(1-methylethyl)-2-oxazoidinone (formula XXIV of Chart C: $R_1$ is cyclopentylazino, $R_{10}$ is isopropyl)

If cyclopentanone is substituted for acetone in the above preparation and the title compound is obtained as yellow micro needles from benzene having a melting point of 154°–159° C.

Analysis calculated for $C_{21}H_{26},N_4O_3$: C, 65.95; H, 6.85; N, 14.65. Found: C, 65.76; H, 6.86; N, 14.51.

The title compound of Example 11 is also prepared using 3.2 grams of the 1-thio analog of Example 17 and 60 mL of hydrazine hydrate which are stirred and refluxed in 120 ml of ethanol under a nitrogen atmosphere for 48 hours. The solvent is removed, ethanol added and the solution stripped again. This is repeated twice. The residue is dissolved in acetone with one ml of acetic acid and is refluxed for three hours. After cooling and stirring with anhydrous potassium carbonate the mixture is filtered and the solvent removed in vacuo. The residue crystallized using activated charcoal from benzene furnishes the produce in 77 percent overall yield from the 1-hydroxy compound.

Example 13

5-[1,2-dihydro-1-(1-methylethyl)azinoisoquinolin-5-yloxymethyl]-3-(1,1-dimethylethyl)-2-oxazolidinone Using the t-butyl analog of the compound in Example 12, the title compound is prepared as tiny yellow crystals from benzene having a melting point of 210° to 213° C.

Analysis calculated for $C_{20}H_{26}N_4O_3$: C, 64.84; H, 7.08; N, 15.13. Found: C, 65.06; H, 7.10; N, 15.05.

Example 14

1-[1,2-dihydro-1-(1-methylethyl)azino]-isoquinolin-5-yloxy]-3-[(1-methylethyl)amino]-2-propanol (formula XXV of Chart C)

A suspension of 6.20 grams of the title compound Example 11 with 21.2 grams of 87% sodium hydroxide pellets are stirred under a nitrogen atmosphere and refluxed in 600 ml of isopropanol for 16 hours. After cooling, the theoretical amount of hydrochloric acid is added and the suspension is filtered. The filtrate is stripped at 40° C., the residue is dissolved in methylene chloride and washed with a saturated solution of sodium chloride made slightly basic with a 10% sodium carbonate solution. The solution is then filtered through anhydrous potassium carbonate and the solvent evaporated in vacuo. The residue is dissolved in methanol and evaporated yielding 5.63 g (98%) of a yellow powder which is crystallized with a little loss from 10 parts benzene at 0° C. using activated carbon; and yields shiny yellow flakes having a melting point of 123°–125° C.

Analysis calculated for $C_{18}H_{26}N_4O_2$: C,65.43; H,7.93; N,16.96. Found: C,65.58; H,8.07; N,16.62.

Example 15

5-[3-(1-methylethyl)-2-oxo-5-oxazolidinylmethyloxy]-1(2H)-isoquinolinone (Formula XXXI of Chart D: $R_2$ is 3-isopropyl-2-oxazolidone)

A mixture of 6.00 g (0.019 mole) of the title compound in Example 5, 3.39 g (0.21 mole, 10% excess) of 1,5-dihydroxyisoquinoline (J. Amer. Chem. Soc., 69, 1941 [1947]) and 0.77 g (0.019 mole) of powdered sodium hydroxide in 70 ml of DMF is stirred and heated under a nitrogen atmosphere at 115°–120° C. for 3 hours; the solids dissolve. The solution is cooled and solvent is removed at 40° C./2 mm. The residue is dissolved in chloroform washed twice with dilute with sodium hydroxide, twice with hydrochloric acid and once with water, then dried by shaking with a saturated sodium chloride solution and filtered through anhydrous potassium carbonate. Evaporation of the solvent at reduced pressure furnishes oily yellow crystals which are stirred with 100 ml of ether and The yellow powder is filtered off and dried, yielding 3.88 g (67%). Recrystallization from 20 ml of methanol gives a white microcrystalline powder, 3.24 grams (56%), having a melting point of 215°–216° C.

Analysis calculated for $C_{16}H_{18}N_2O_4$: C,63.26; H,6.00; N,9.27. Found: C,63.27; H,5.97; N,9.21.

From the mother liquor of a larger run 5-[3-(1-methylethyl)-2-oxo-5-oxazolidinylmethyloxy]-2-[3-(methylethyl)-2-oxo-5-oxazolidinylmethyl]-1(2H)-isoquinolinone ws obtained as white rosettes after several recrystalizations from ethyl acetate/ether; and has a melting point of 163° to 165° C.

Analysis calculated for $C_{23}H_{29}N_3O_6$: C, 62.29; H, 6.59; N, 9.48. Found: C, 62.43; H, 6.71; N, 9.59.

Example 16

5-[3-(1,1-dimethylethyl)-2-oxo-5-oxazolidinylmethoxy]-1(2H)-isoquinolidinone (formula I of Chart A, $R_4$ is t-butyl)

Using the N-t-butyl analog of the title compound of Example 5 in the process of Example 15 the title compound is prepared and recrystallized using activated carbon from methanol to furnish matted white needles having a melting point of 240°-242° C.

Analysis calculated for $C_{17}H_{20}N_2O_4$: C, 64.53; H, 6.37; N, 8.86. Found: C, 64.68; H, 6.40; N, 8.83.

Example 17

5-[1-mercapto-5-isoquinolinyloxymethyl]-3-(1-methylethyl)-2-oxazolidinone (formula XXXII of Chart D: $R_2$ is 3-isopropyl-2-oxazolidione)

A mixture of 1.0 g of the title compound of Example 15 and 1.0 g of $P_2S_5$ is refluxed under a nitrogen atmosphere and 50 ml of pyridine for two hours. The solvent is removed in vacuo. The residue stirred with dilute hydrochloric acid and the yellow powder filtered off, washed well with water, and dried. This material was sufficiently pure for further reaction; a portion is crystallized twice from a large volume of methanol to furnish shining yellow plates having a melting point of 237°-239° C.

Analysis calculated for $C_{16}H_{18}N_2O_2S$: C, 60.26; H, 5.70; N, 8.80; S, 10.17. Found: C, 60.23 H, 5.65; N, 8.81; S, 10.13.

Example 18

5-[(1-mercapto-5-isoquinolinyl)oxymethyl]-3-(1,1-dimethylethyl)-2-oxazolidinone (formula XXXII of Chart D: $R_{10}$ is t-butyl)

Using the method described in Example 17 and using appropriate starting materials the title compound is prepared and recrystallized from dimethylsulfoxide-$H_2O$ as a yellow powder having a melting point of 264°-269° C.

Analysis calculated for $C_{17}H_{20}N_2O_3S$: C, 61.42; H, 6.06; N, 8.42; S, 9.64. Found: C, 61.00; H, 6.08; N, 8.27; S, 10.05.

Example 19

5-[3-(2-[3,4-dimethoxyphenyl]ethyl)-2-oxo-5-oxazolidinylmethyloxy]-1(2H)-isoquinolinone (formula XXXI of Chart D $R_2$ is of formula III, $R_{10}$ is 2(3,4 dimethoxyphenyl ethyl)

Using the appropriate starting materials and the previously described process, the title compound is prepared having a melting point of 173°-175° C. after recrystallization from methanol-water.

Example 20

5-[1,2-dihydro-1-(1 methylethyl)azino-5-isoquinolinyloxymethyl]-3-[2-(3,4-dimethoxyphenyl)ethyl]-2-oxazolidinone (formula XXIV of Chart C, $R_1$ is =N—N=$R_4$, $R_{10}$ is 2 (3,4-dimethoxyphenyl) ethyl, $R_4$ is isopropylidene)

Using the appropriate starting materials and the previously described Process, the title compound is prepared, having a melting point of 138°-142° C. after recrystallization from benzene-ether.

Example 21

1-[1,2-dihydro-1-(1-methylethyl)azino-5-isoquinolinyloxy]-3-[2-(3,4-dimethoxyphenyl)ethylamino]-2-propanol (formula XXV of Chart C, $R_1$ is =N—N=$R_4$, $R_4$ is isopropylidine, $R_7$ is H, $R_8$ is H, and $R_9$ is 2-(3,4-dimethoxyphenyl-ethyl)

Using the appropriate starting materials and the process above the title compound is prepared having a melting point of 90°-92° C. after recrystallization from ether.

CHART A

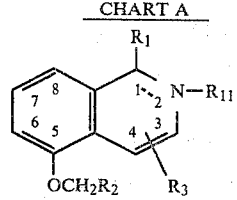  I

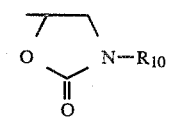  II

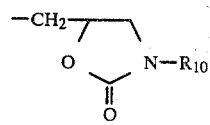  III

CHART B

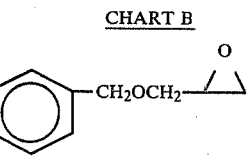  XI

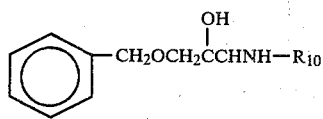  XII

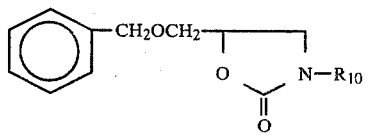  XIII

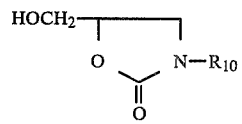  XIV

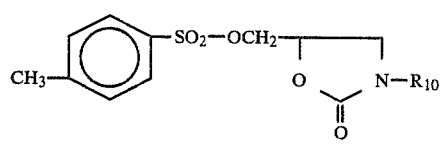  XV

CHART C

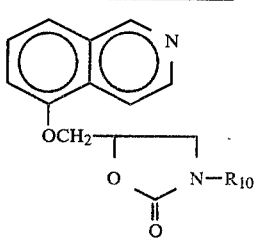  XXI

-continued
CHART C

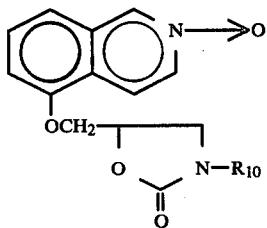
XXII

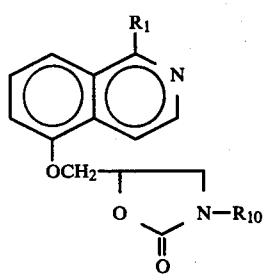
XXIII where R₁ is halogen

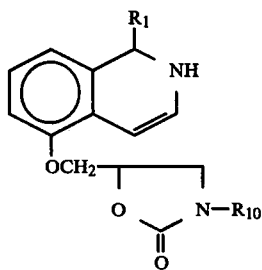
XXIV where R₁ is —NH—NH₂, =N—N=R₄ or alkyl

-continued
CHART C

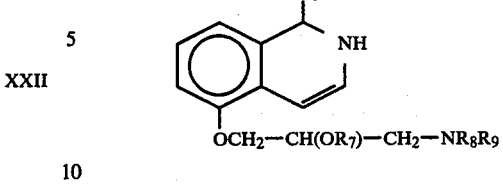
XXV

CHART D

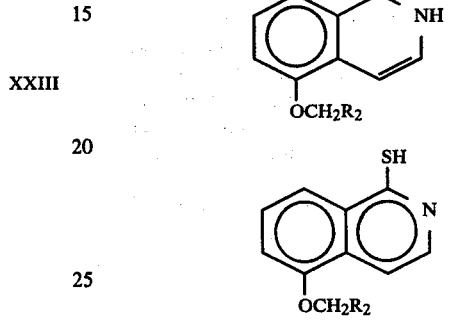
XXXI

XXXII

I claim:
1. 5-[1,2-dihydro-1-(1-methylethylazino)-5-isoquinolinylmethyl]-3-(1-methylethyl)-2-oxazolidinone.
2. 1-[1,2-dihydro-1-(1-methylethylazino)-5-isoquinolinyloxy]-3-(1-methylethylamino)-2-propanol.
3. 5-[1-(Cyclopentylazino)-1,2-dihydro-5-isoquinolinyloxymethyl]-3-(1-methyl-ethyl)-2-oxazolidinone.
4. 5-[1,2-dihydro-1-(1-methylethylazino)-5-isoquinolinyloxymethyl]-3-[2-(3,4-dimethyloxyphenyl)ethyl]-2-oxazolidinone.
5. 1-[1,2-dihydro-1-(methylethylazino)-5-isoquinolinyloxy]-3-[2-(3,4-dimethyoxyphenyl)ethylamino]-2-propanol.

* * * * *